(12) United States Patent
Yachia et al.

(10) Patent No.: US 6,293,923 B1
(45) Date of Patent: *Sep. 25, 2001

(54) INTRAVESICULAR BALLOON

(75) Inventors: Daniel Yachia, Herzliya onSea; Eran Hirszowicz, Ramat-Chen, both of (IL)

(73) Assignee: Innoventions, Inc., Edina, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/268,109

(22) Filed: Mar. 15, 1999

(51) Int. Cl.[7] ............ A61M 29/00; A61M 11/00; A61F 2/00

(52) U.S. Cl. .................. 604/96.01; 604/93.01; 600/29

(58) Field of Search ............... 604/93, 96, 500, 604/502, 509, 517, 514, 285, 890.1–892.1; 600/29, 30, 31; 128/885, DIG. 25

(56) References Cited

U.S. PATENT DOCUMENTS

| | | |
|---|---|---|
| 4,258,705 | 3/1981 | Sorensen et al. .............. 128/1 R |
| 4,834,704 * | 5/1989 | Reinicke .................... 604/51 |
| 4,850,963 | 7/1989 | Sparks et al. ................ 600/29 |
| 4,871,542 | 10/1989 | Vilhardt ..................... 424/423 |
| 4,925,446 * | 5/1990 | Garay et al. ................. 604/96 |
| 5,019,032 * | 5/1991 | Robertson ................... 600/29 |
| 5,030,199 | 7/1991 | Barwick et al. .............. 600/29 |
| 5,188,109 | 2/1993 | Saito ........................ 128/635 |
| 5,234,409 | 8/1993 | Goldberg .................... 604/96 |
| 5,443,470 * | 8/1995 | Stern et al. ................. 607/98 |
| 5,513,659 | 5/1996 | Buuck et al. ................ 128/885 |
| 5,579,781 | 12/1996 | Cooke ....................... 128/733 |
| 5,604,531 | 2/1997 | Iddan et al. ................. 348/76 |
| 5,704,353 | 1/1998 | Kalb et al. .................. 128/634 |
| 5,749,845 * | 5/1998 | Hildebrand et al. ........... 604/21 |
| 5,806,527 * | 9/1998 | Borodulin et al. ............ 128/885 |
| 5,984,860 * | 11/1999 | Shan ......................... 600/116 |
| 6,039,967 | 3/2000 | Ottoboni et al. .............. 424/426 |
| 6,139,535 * | 10/2000 | Greelis et al. ................ 604/500 |

FOREIGN PATENT DOCUMENTS 0667115    8/1995   (EP) .

* cited by examiner

Primary Examiner—Richard K. Seidel
Assistant Examiner—Michael J. Hayes
(74) Attorney, Agent, or Firm—Ladas & Parry

(57) ABSTRACT

An expandable balloon for insertion into the urinary bladder of an individual. The balloon may be used in treating the urinary bladder, in monitoring the urinary bladder or in the treatment of urinary incontinence.

33 Claims, 13 Drawing Sheets

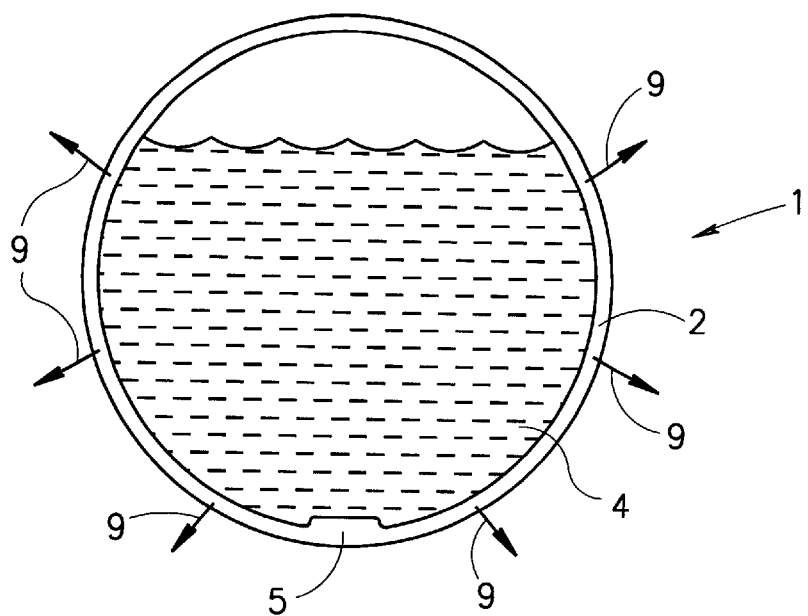
FIG. 6
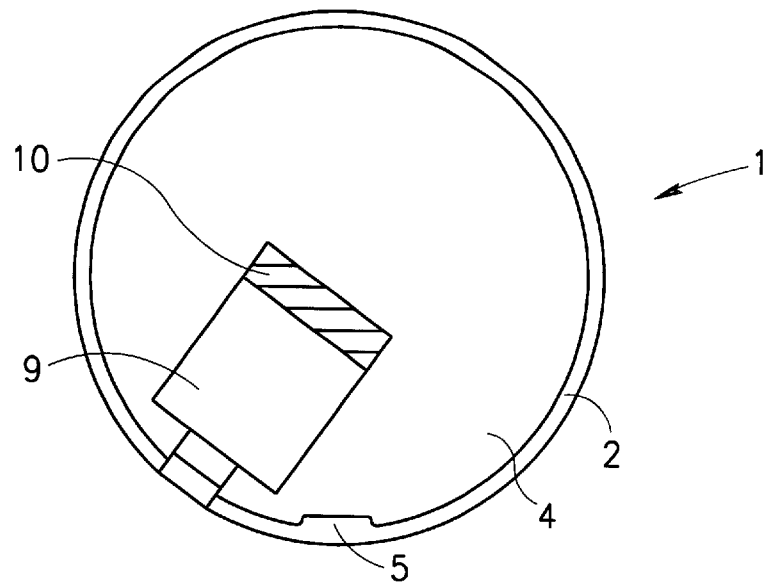
FIG. 7
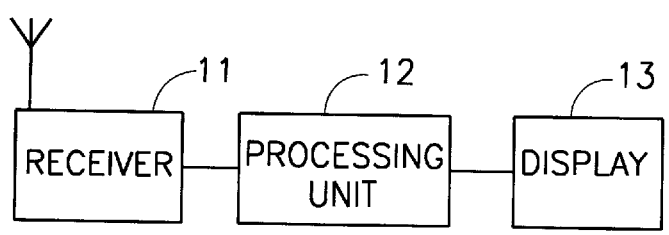

INTRAVESICULAR BALLOON

FIELD OF THE INVENTION

The invention is in the field of medical devices. More specifically, the invention relates to devices for the treatment of urinary bladder disorders.

BACKGROUND OF THE INVENTION

Several disorders of the urinary tract are known. Among these are urinary incontinence, chronic urinary tract infections, urinary bladder tumors.

Urinary Incontinence

Urinary incontinence mostly affects women (approximately 10 million in the U.S.A. alone) primarily after childbirth or due to old age. In men, urinary incontinence often occurs as a complication of surgery or old age (approximately 3 million in the U.S.A.).

Incontinence has serious economic, health, social and psychological consequences. Its estimated cost to the health system in the United States in 1993 was U.S. 16 billion. It leads to chronic and severe skin irritation in the genital area, an increase in urinary infections and urosepsis. Fear of incontinence and odors in public cause incontinent people to severely restrict their social activities. The impact on the mental health of the affected people may be even more devastating than the social and health consequences. They suffer severe embarrassment, loss of self-esteem, depression and anxiety.

Urinary incontinence can be divided into 4 groups:

Stress Incontinence—is the involuntary release of urine due to a sudden increase in the intraabdominal pressure caused by laughing, sneezing, coughing, running, etc. This is the most common type of incontinence and in women may be the result of childbirth, estrogen deficiency, unsuccessful surgical repairs for incontinence or pelvic irradiation. In men, it often happens after surgery for benign enlargement of the prostate gland or after radical removal of the prostate.

Total Incontinence—is the continuous leak of urine entering the bladder due to failure of the sphincteric muscles.

Urge Incontinence—is involuntary loss of urine due to involuntary bladder contractions. This type of incontinence mostly affects the elderly who leak until they reach a toilet.

Mixed Incontinence—is a combination of stress and urge incontinence. This condition is more common in elderly women than men.

Ideally, treatment of incontinence should provide permanent dryness and is easy to perform.

Pharmacological treatments of bladder dysfunctions are based either on estrogen replacement for treating postmenopausal vaginal and urethral atrophy or on agents affecting the tonus of the bladder muscle. Since affected elderly women suffer from both hormonal deficiency and urge incontinence, both types of agents are usually prescribed simultaneously.

Surgical treatments are based on restoring the anatomical changes causing the incontinence. Although in the short-term most surgical procedures restore continence, the long-term prognosis is usually unsatisfactory. Moreover, surgery entails morbidity and high expenses.

Conservative/behavioral treatments are based on pelvic floor muscle exercises, bladder training, biofeedback, vaginal cones, low-frequency electrostimulation of pelvic floor muscles, intravaginal bladder neck support pessaries, urethral meatus suction cups and intraurethral devices. Conservative treatments are time consuming and require the patients' understanding, cooperation and persistence.

Devices which have been used to obtain almost immediate dryness in incontinent people can be divided into two groups:

(1) Urethral Plugs/Inserts

These comprise a flexible rod having a 14 Ch. (approximately 4.5 mm) diameter and a length adjusted to fit the length of the patient's urethra. The rod has an inflatable balloon on its bladder end and a flange at other end. After insertion of the device, the balloon is inflated in the bladder. The balloon and the flange maintain the device in its proper position within the urethra. The balloon and rod form a mechanical barrier to retain the urine within the bladder. The balloon must be deflated and the device removed and discarded prior to voiding. Such inserts are known in the art, for example, the device known as RELIANCE™ produced by UroMed Corp., U.S.A.

Since the inserts are discarded after each voiding and replaced with a new one by the patient, manual dexterity of the patient is required. Insertion of an insert into a female has the risk of pushing vaginal and perineal bacteria into the bladder and insertion of an insert a few times a day increases this risk. The inconvenience of removing and inserting a new device and its costs, in addition to the infection risk, are the major disadvantages of these devices.

(2) Valve Catheters

These comprise a tube with a valve at one end. The bladder end of the device typically has a balloon or flanges for retaining the device in place and a flange at the other end to prevent migration into the bladder. The valve is opened for voiding through the lumen of the catheter with the help of an external magnet. The tube typically has a 18 Ch. (6 mm.) to 20 Ch. (approximately 7 mm) diameter and a length adjusted to fit the patient's urethra. For male incontinence, an active intraurethral Foley-type catheter is used. This device has a retaining balloon at its bladder end and another smaller balloon under the prostate for fixing the device in place. The magnet activated valve is situated at the end of the device near the distal end of the urethra. Active inserts are typically left indwelling up to 4 weeks and are then replaced. Examples of such catheters are disclosed in U.S. Pat Nos. 5,030,199 and 5,234,409.

Valve catheters are more convenient for the patient than the inserts. However, in females they cause ascending infection because they connect the bladder with the vulva which is rich in pathogenic bacteria, especially *Escherichia Coli*. Even with continuous use of antibiotics, infection is unpreventable in the majority of cases.

During prolonged use of catheters or inserts in female patients, a relaxation of the urethra occurs and the patients may start to leak around the device. Unfortunately valve catheters and inserts are unavailable in increasing diameters.

A significant disadvantage of both the inserts and the valve catheters is the discomfort felt by the patient especially when sitting and during sexual intercourse (felt by the patient and the partner). The present invention therefore provides a device for the treatment of urinary incontinence in which the disadvantages of the prior art devices are substantially reduced or eliminated.

Urinary Tract Infections

Nearly half of all women experience urinary tract infection (UTI) at some point in their lifetime and most of these infections are confined to the bladder. Isolated UTIs can be treated by short and effective antibiotic treatment. However, recurrent UTIs often occur in women due to antibiotic resistant bacteria. In this case complicated infections often exhibit multidrug resistance and necessitate longer antimicrobial drug administrations.

Treatment of UTI often requires urinary levels of antimicrobial drugs that are several hundred times greater than those allowable in the blood. Many antibacterials cannot be used in UTI because, when taken orally or intravenously, they do not attain the required concentration in the urine, without exceeding the allowable limit in the blood. It would therefore be desirable to be able to continuously introduce antimicrobial drugs continuously and directly into the bladder.

Bladder Tumors

Even after resection, bladder tumors may not only recur but may also invade deeper in the bladder wall. Due to the heterogenity of these tumors (from low-grade tumors showing a benign course to highly malignant high-grade tumors), there does not exist a single approach to the surveillance and treatment of these tumors. Intravesical drug therapies are often used for reducing tumor recurrence. In this approach, an immunotherapeutic or chemotherapeutic agent is inserted into the bladder through a catheter. This treatment is typically repeated once a week for 6 weeks and then once a month for a period of 6–12 months. However, periodic treatment has not been established as being effective in altering the progression of the tumor. Continuous local treatment with chemotherapeutic or radioactive materials may treat or prevent not only superficial tumors but also deep tumors as well. It would therefore be desirable to be able to introduce antitumoral drugs continuously and directly into the bladder.

Bladder Dysfunction

During filling, the bladder muscle relaxes for keeping the intravesical pressure low while it contracts for voiding. Certain diseases such as spinal cord injuries, diabetes, multiple sclerosis, or hormonal changes after menopause or old age in both sexes may cause a hypo contractility or, paradoxically, hyper contractility of the muscle. In atonic bladder, pharmacological treatment is not very effective. In hyperreflexic bladder, drugs for relaxing the bladder cause constipation and mouth dryness and are therefore not tolerated well by the patients.

Diagnosis of bladder dysfunction requires continuously monitoring various bladder parameters during filling and/or voiding. These measurements usually are made by inserting a catheter connected to a measuring device into the bladder. This is done, for example, in uroflowmetry (measurement of urinary flow rate) which is non-invasive, simple and inexpensive. However, its sensitivity and specificity are low. Cystometry is an invasive technique for measuring bladder capacity, compliance and muscle tonus. Pressure-flow study is an invasive and costly test for distinguishing patients with low urinary flow due to obstruction or bladder antonia, from those with high intravesical pressure and high urinary flow. It is therefore a need in the art for a simple and inexpensive technique for intravesicular monitoring.

In the diagnostic procedure known as "urodynamics", the bladder is filled through a catheter, and the response of the bladder is monitored. Available 24 hour urodynamic monitors have catheters or wires passing through the urethra, connecting sensors inserted into the bladder to a recorder. The connecting wires and catheters inadvertently introduce pathogenic bacteria from the genital areas into the bladder. It is therefore desirable to be able to monitor bladder function over several cycles of filling and voiding without the need for such wires or catheters.

Diagnosis of some intravesical pathological conditions often involves inserting an endoscope into the bladder and optically scanning the bladder walls. In cases of bleeding in the ureters or the kidneys, the observation of blood coming through the ureteral orifices allows determination of the origin of the bleeding. However, if the bleeding has temporarily stopped at the time of the examination, or if the blood concentration in the urine is insufficient to make the urine red or pink, endoscopy is of little value in reaching a diagnosis. In such cases more invasive procedures are performed in order to enter the upper urinary tract. It is therefore desirable to be able to monitor the bladder over long periods of time.

Bladder shape during filling and its contraction during voiding is important for the diagnosis of certain bladder pathologies. These functions can be followed in fluoroscopy and by sonography. These techniques however are not accurate and cannot be used for monitoring changes in bladder shape over long periods of time. It would therefore be desirable to be able to continuously image the bladder interior over long periods of time.

The present invention therefore provides a device for continuous monitoring of the bladder interior and for the treatment of bladder disorders in which the disadvantages of the prior art devices are substantially reduced or eliminated.

SUMMARY OF THE INVENTION

The present invention provides a system comprising an expandable balloon to be inserted into the urinary bladder. The balloon may be filled and compressed prior to insertion and then allowed to expand after insertion in the bladder. Alternatively, the balloon may be filled after insertion so as to expand in the bladder.

The invention may be used for the intermittent sealing of the urinary bladder outlet and the prevention of involuntary urine leakage. Sealing the urinary bladder outlet involves lodging the balloon in the outlet so as to seal it. Unsealing the outlet to allow voiding of the bladder involves dislodging the balloon from the outlet.

The invention may also be used for such purposes as for example, delivery of drugs, imaging the urinary bladder, and measuring intravesicular parameters such as pressure in the urinary bladder. When used for such purposes, the balloon may be, for example, lodged in the urinary bladder outlet, immobilized in some other desired location in the bladder, freely floating in the urine in the bladder, etc.

The invention is entirely confined to the urinary bladder and has no urethral parts. As will become apparent in the description below, the balloon is easily inserted and removed. It may be left in the bladder for prolonged periods of time without encrusting or causing infections and is displaced within the bladder at will using a hand held magnet. The invention is comfortable for the patient and does not interfere with the daily activities of the patient including sitting, jogging, riding, or sexual intercourse.

The invention thus provides an expandable balloon for insertion into the urinary bladder of an individual, the balloon having a wall and a lumen and formed with a magnetable portion.

The invention also provides a system comprising the balloon together with an applicator for inserting and retrieving the balloon, a displacing member for displacing the balloon within the bladder, and an immobilizing member for immobilizing the balloon at a desired location in the bladder.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 6 shows a balloon comprising diffusible substances within its wall or lumen;

FIG. 7 shows a balloon comprising a microvideo camera;

DETAILED DESCRIPTION OF SPECIFIC EMBODIMENTS

Figure 1A:
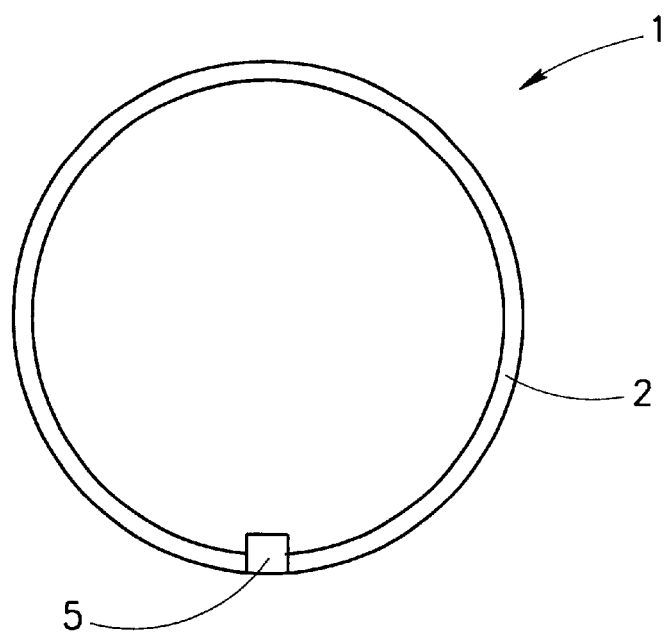
FIGS. 1(A–D) show various embodiments of the balloon according to the invention.
Figure 1B:
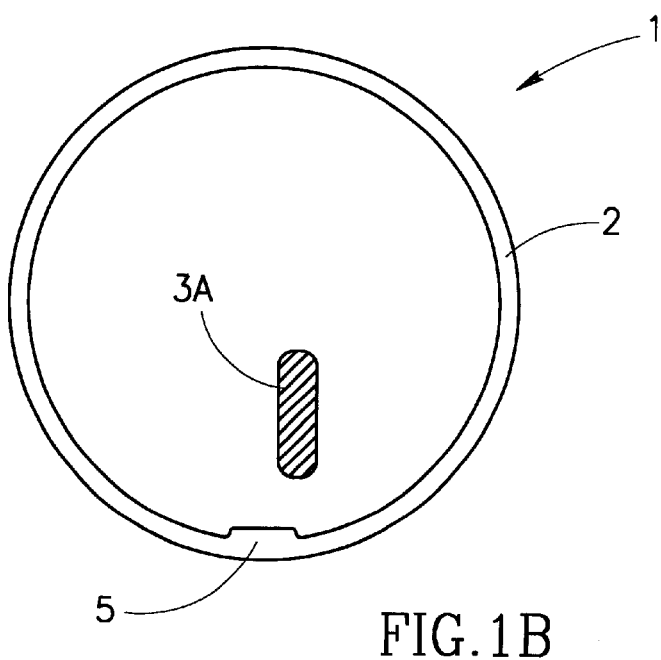
Figure 1C:
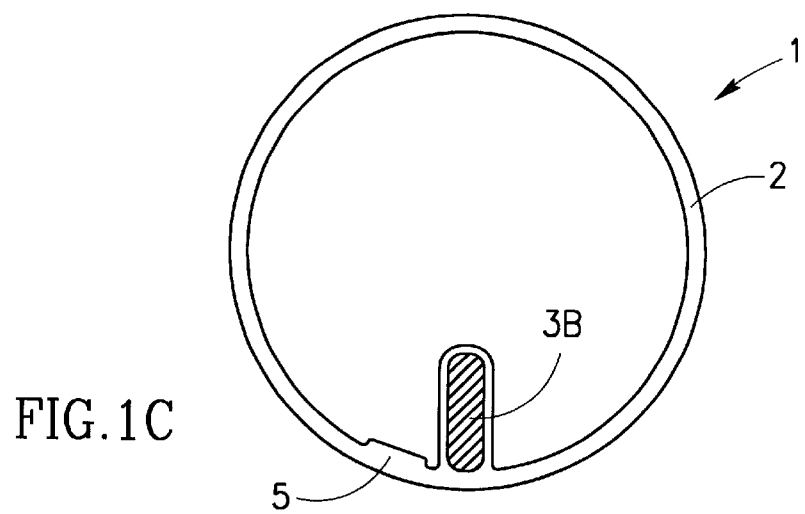
Figure 1D:
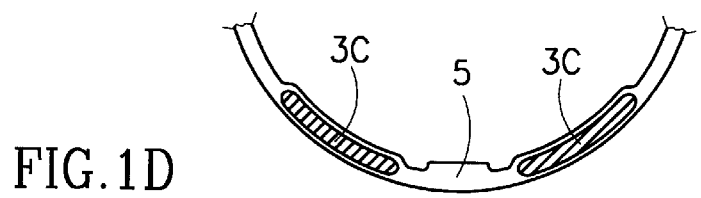

Reference is now made to FIG. 1 which shows several embodiments of the invention. An expandable hollow balloon generally designated as 1 has a wall 2 made of an elastic biocompatible material enclosing a lumen 4. The balloon 1 may further comprise a magnetable portion which may consist for example, of one or more metal particles which may be free in the lumen 3a (as in FIG. 1b), attached to the inner surface 3b (as in FIG. 1c) or embedded in the wall 3c of the balloon (as in FIG. 1d). The lumen 4 of balloon 1 may be filled with a biocompatible fluid which may be presterilized such as air, water, saline or an oil such as liquid paraffin.

Figure 2:
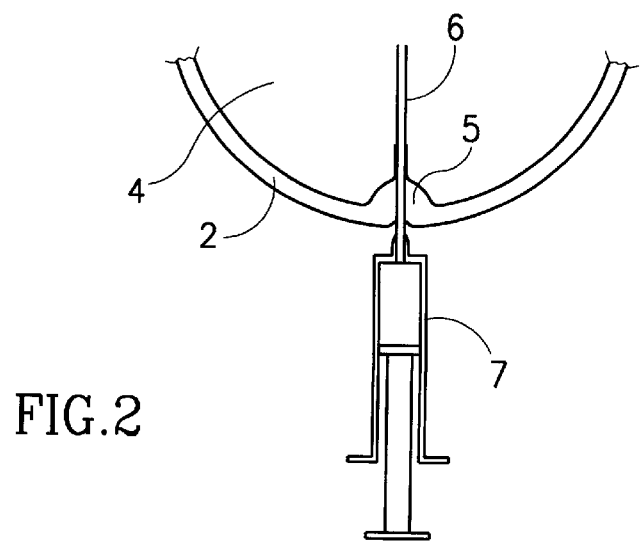
FIG. 2 shows a portion of a balloon according to the invention having a duck-bill valve.
Figure 3A:
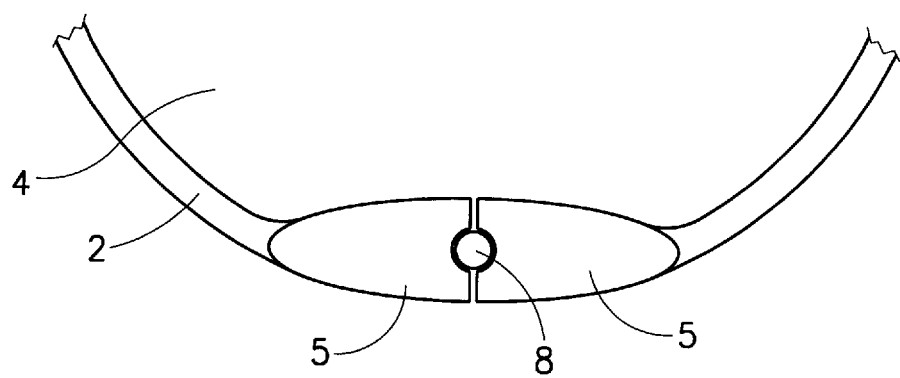
FIGS. 3(A,B) show a portion of a balloon according to the invention having a ball valve.
Figure 3B:
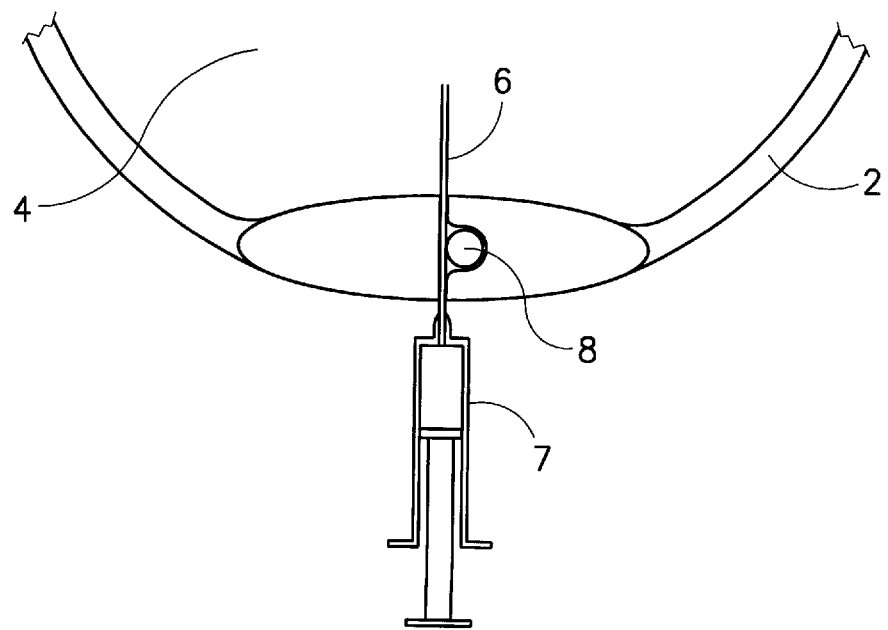

A self-sealing valve 5 in the wall of the balloon is used to fill the balloon. The valve 5 may be for example a duck-bill type valve as shown in FIG. 2 or a ball valve as shown in FIG. 3 in which a ball 8 may be in a sealing position (FIG. 3a) or an unsealing position (FIG. 3c). The canula 6 of a syringe 7 is inserted through the valve 5 into the lumen 4 of the balloon. The fluid injected into the lumen 4 causes the balloon to expand. After filling, the syringe needle 6 is withdrawn, and the valve 5 seals itself. After filling, the balloon may adopt a predetermined shape, for example, a sphere, ellipsoid, or an irregular shape. The filled inflated balloon may float or sink in urine.

Figures 4A, 4B:
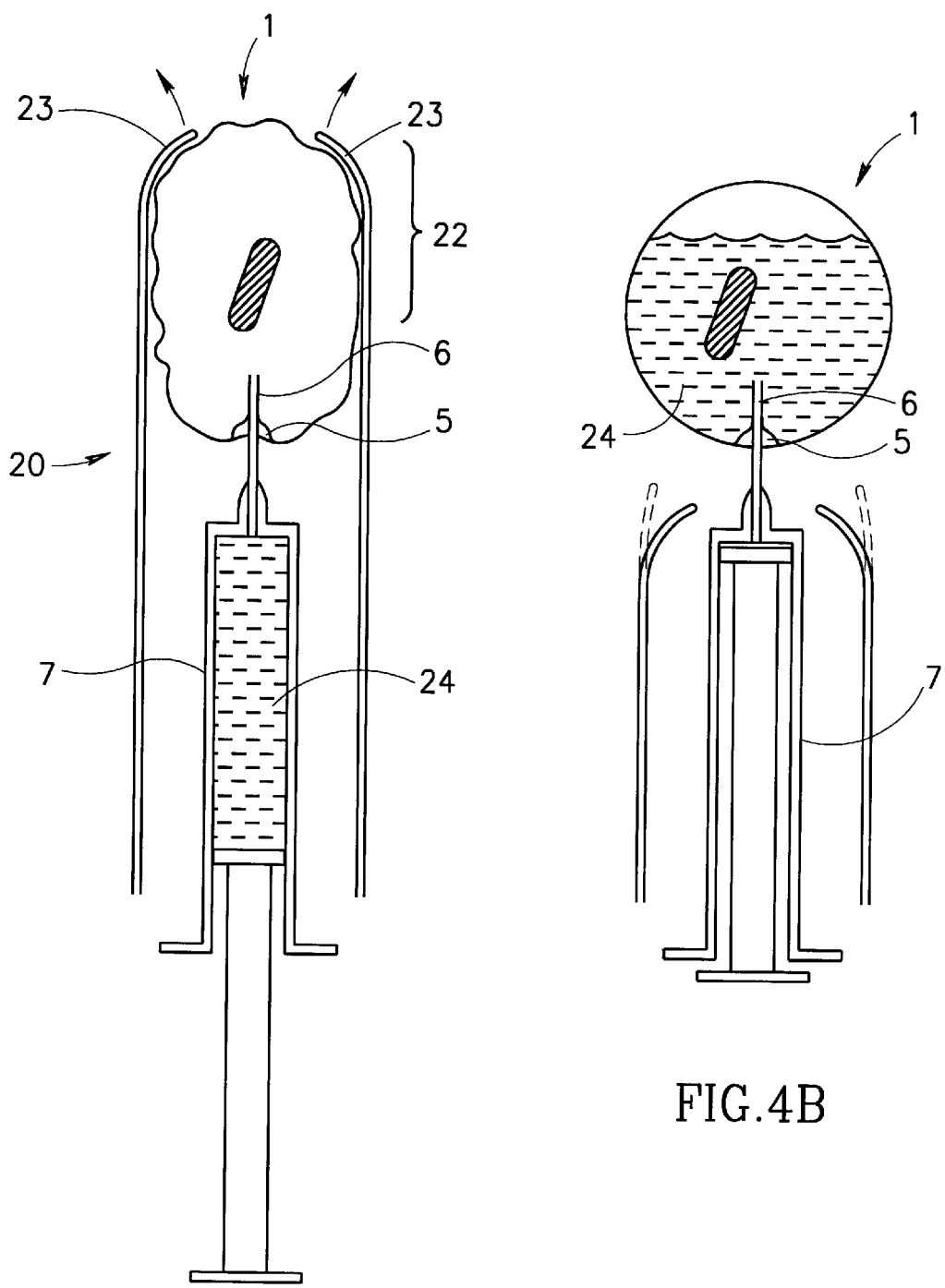
FIGS. 4(A,B) show a balloon filled after have been inserted into the urinary bladder.
Figures 5A, 5B:
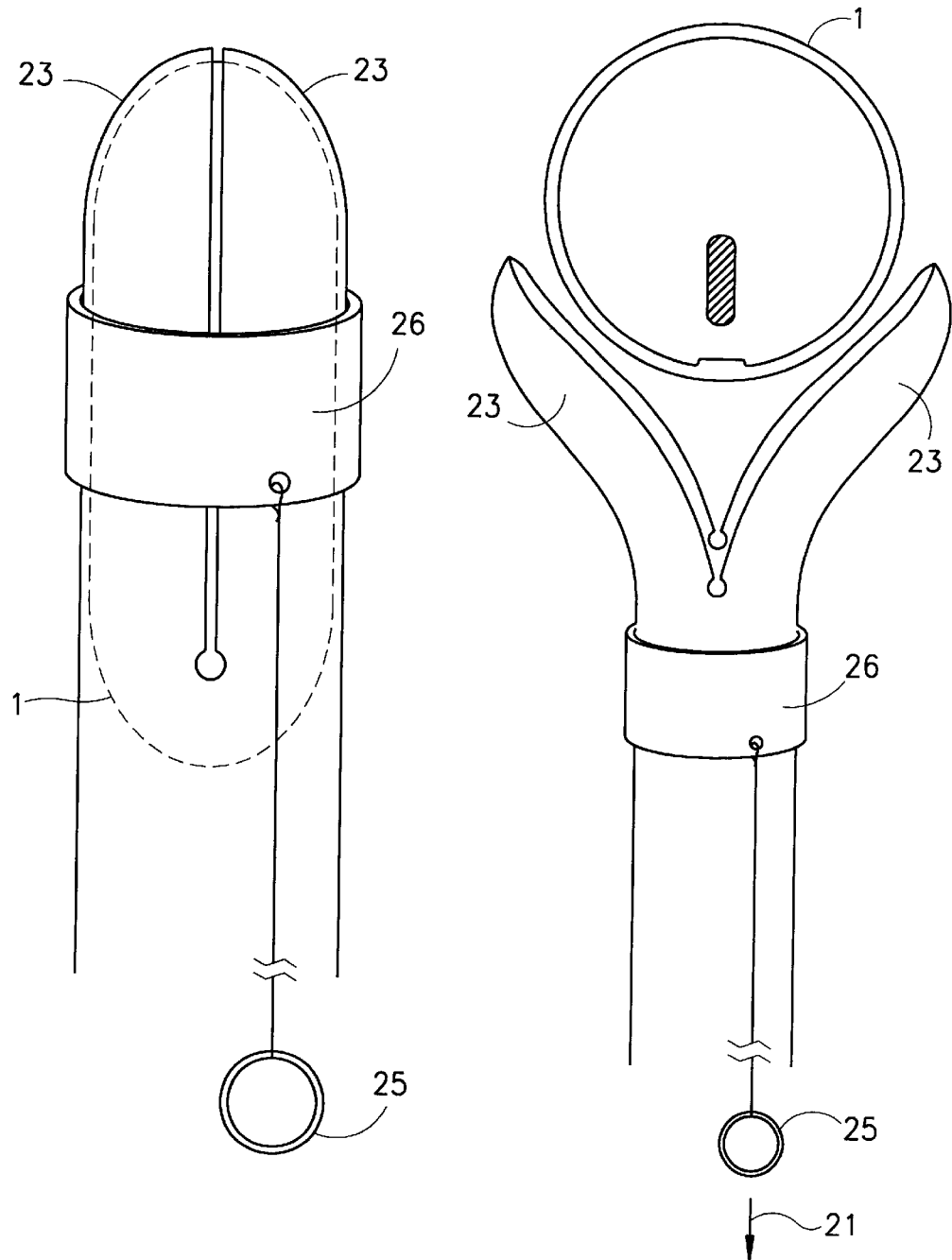
FIGS. 5(A,B) show a balloon filled before being inserted into the urinary bladder.

As shown in FIG. 4, the balloon may first be inserted into the bladder by means of an applicator 20 to be described below in detail (FIG. 4a) and following its release from the applicator into the bladder, the balloon is then filled with fluid 24 from a syringe 7 (FIG. 4b). Alternatively, as shown in FIG. 5a, the balloon 1 may be filled and compressed before being inserted into the bladder by means of applicator 20. The prefilled balloon is clutched by the flanges 23 which are initially kept closed by constraining sleeve 26 (FIG. 5a). After insertion of the applicator 20 with the prefilled balloon 1 into the urinary bladder, ring 25 is pulled as indicated by arrow 21 in FIG. 5b to urge the constraining sleeve 26 away from the flanges 23, allowing flanges 23 to open and release the prefilled balloon 1 into the bladder.

FIG. 6 shows a balloon 1 constructed so as to have one or more diffusible substances contained within its wall 2 or lumen 4. Such substances could be, for example, drugs, antibiotics immunoglobulins, or radioactive substances, etc. After insertion of the balloon 1 into the lumen of the urinary bladder, the substances diffuse from the balloon 1 into the bladder (arrows 9) in order to achieve a desired effect.

FIG. 7 shows a balloon 1 constructed so as to comprise a microvideo camera 19 for imaging the interior of the bladder. The video camera 19 may have associated with it a transmitter 10 for transmitting images to a remote receiver 11. Such microvideo cameras and transmitters are known in the art, for example, as disclosed in U.S. Pat. Nos. 5,604,531, 5,579,781 and 5,188,109. The receiver 11 may be connected to a processing unit 12 for processing the images, or a display 13 for displaying images.

Figure 8:
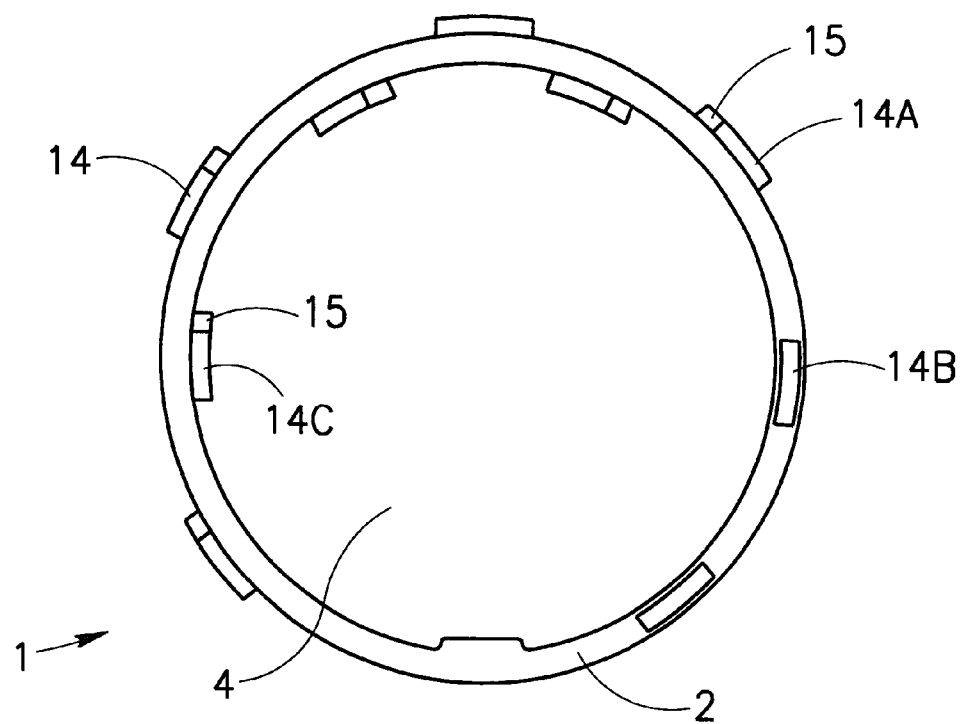
FIG. 8 shows a balloon comprising devices for measuring urinary bladder parameters.
Figure 8:
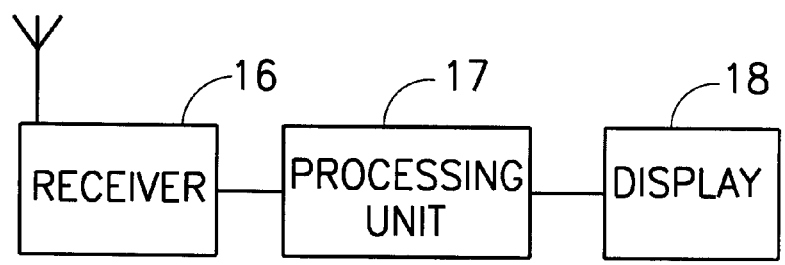

FIG. 8 shows a balloon 1 constructed so as to comprise one or more devices 14 for measuring one or more parameters associated with the urinary bladder, for example, bladder pressure, urine temperature, urine density, urine conductivity or urine composition. The devices 14 may be affixed to the outer surface of the balloon 14a, embedded within the wall 2 of the balloon 14b or affixed to the inner surface of the balloon 14c. The measuring devices 14 may have associated with it a transmitter 15 for transmitting measurements to a remote receiver 16. The receiver may be connected to a processing unit 17 for processing the measurements or to a display 18 for displaying results. Such measuring devices are known in the art, for example as disclosed in U.S. Pat. Nos. 5,579,781 and 5,188,109.

Figure 9:
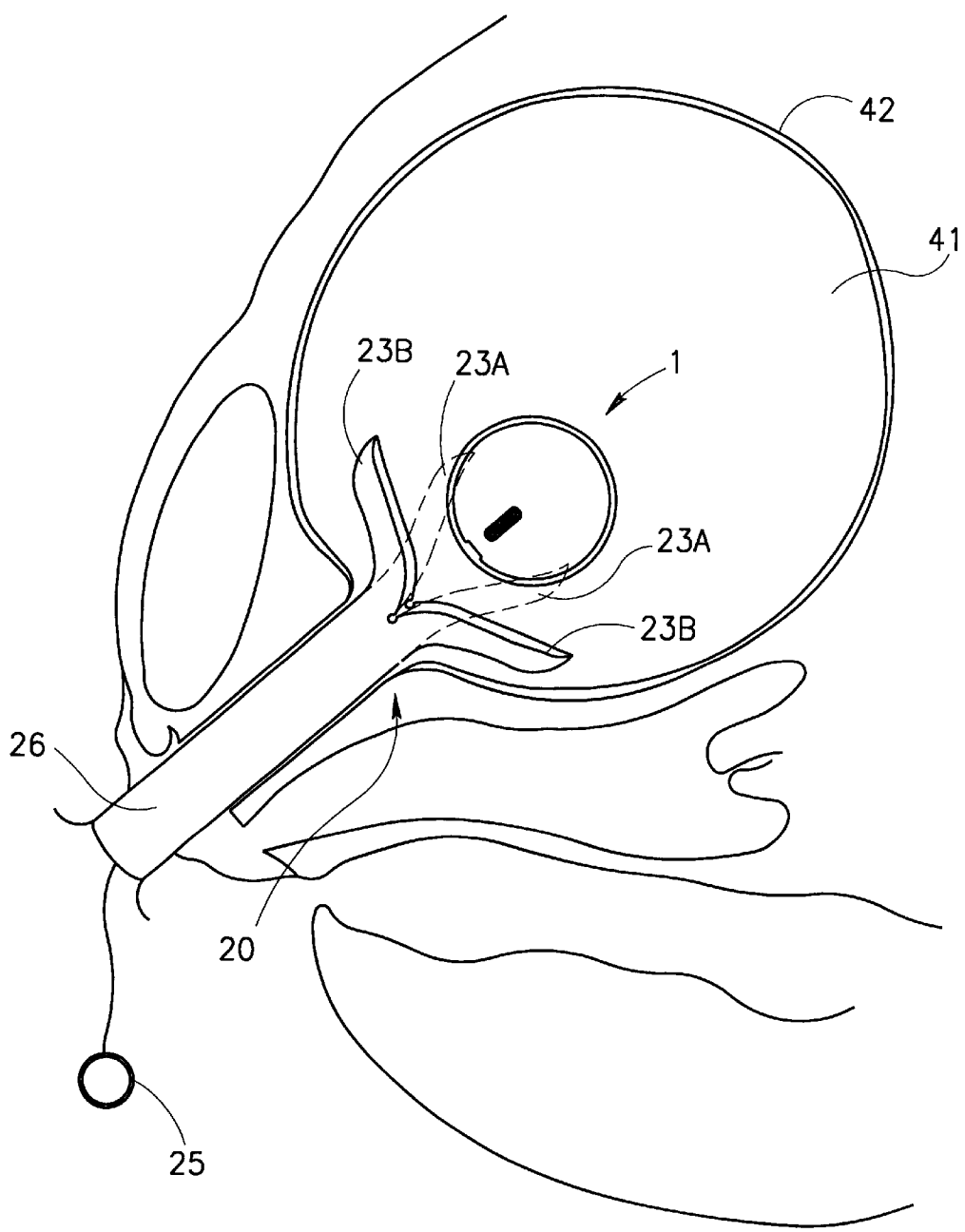
FIG. 9 shows use of an applicator for inserting a balloon into the urinary bladder of a female individual.
Figure 10:
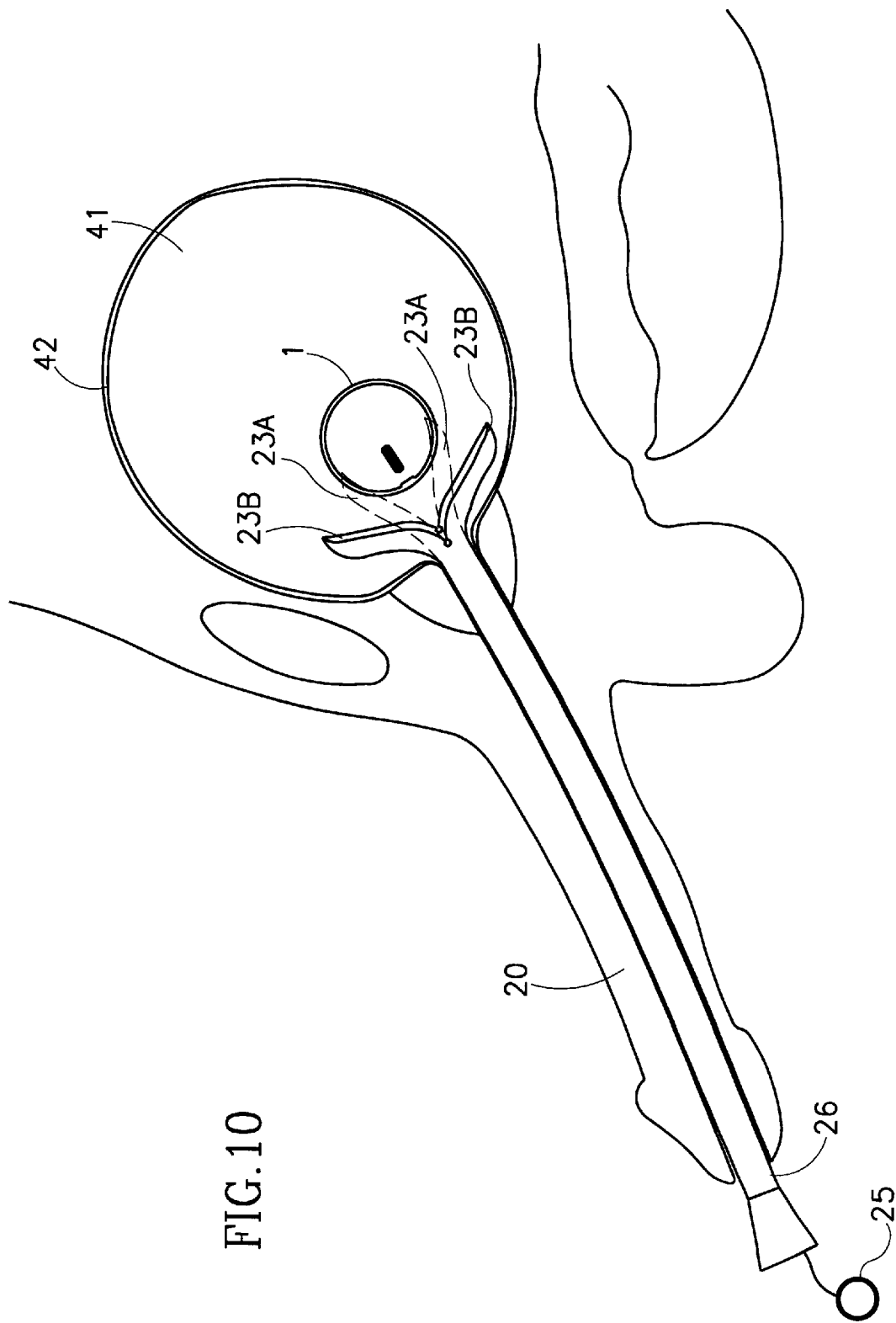
FIG. 10 shows use of an applicator for inserting a balloon into the urinary bladder of a male individual.

FIG. 9 shows use of an applicator 20 for inserting the balloon 1 into the lumen 41 of the urinary bladder 42 of a female individual, and FIG. 10 shows use of the applicator 20 inserting the balloon 1 into the lumen of the urinary bladder 42 of a male individual. In either case the balloon 1 is initially grasped by the closed flanges 23a at the distal end of the applicator 20 (FIGS. 9a and 10a). The distal end of the applicator-balloon combination is inserted into the urethra until it reaches the lumen 41 of the bladder 42. The balloon 1 is then released from the applicator by opening the flanges 23b by pulling on ring 25 while holding the constraining sleeve 26. The applicator 20 is then removed from the body, leaving the balloon 1 in the bladder lumen 41.

Figure 11:
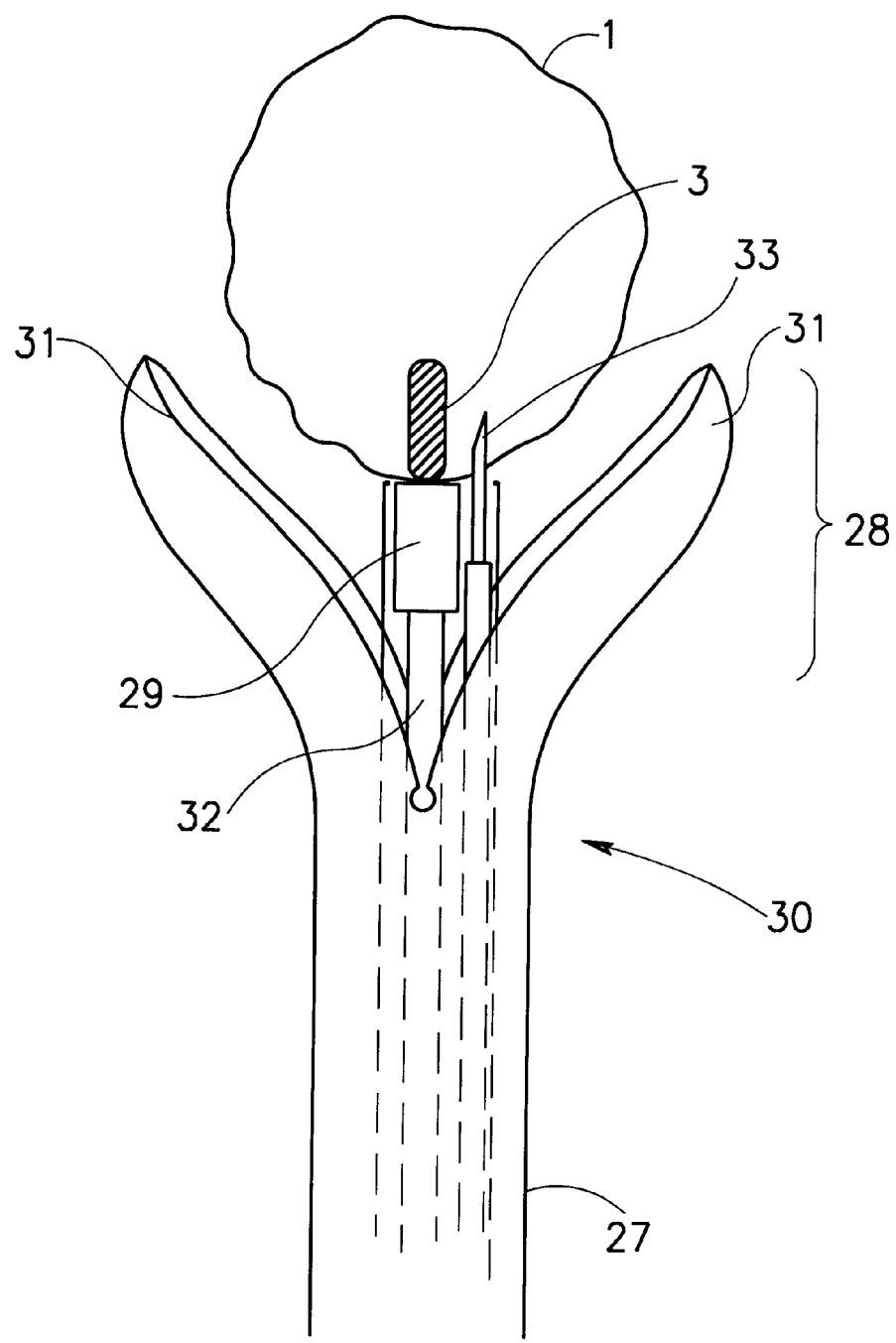
FIG. 11 shows a retrieval device for retrieving a balloon.

FIG. 11 shows a retrieval device generally designated as 30 for removing the balloon from the bladder. A catheter 27 has at its distal end 28 a magnetable portion 29 so as to hold the balloon 1 at the distal tip 28 by means of the magnetable particles 3 associated with the balloon 1.

The retrieval device is inserted into a full bladder. After opening the flanges 31 of the retrieval device, the engaging probe 32 with magnetable portion 29 in its tip is inserted into the lumen of the full bladder so as to engage the magnet 3 of the balloon and push the balloon into the lumen of the bladder. The probe 32 is then pulled so as to bring the balloon 1 into the grip of flanges 31 of the retrieval device. A piercer 33 is inserted into the balloon to drain the fluid contained in its lumen 4 into an attached syringe (not shown) or into the bladder lumen. The applicator 20 is then withdrawn from the patient together with the deflated balloon 1.

Figure 12:
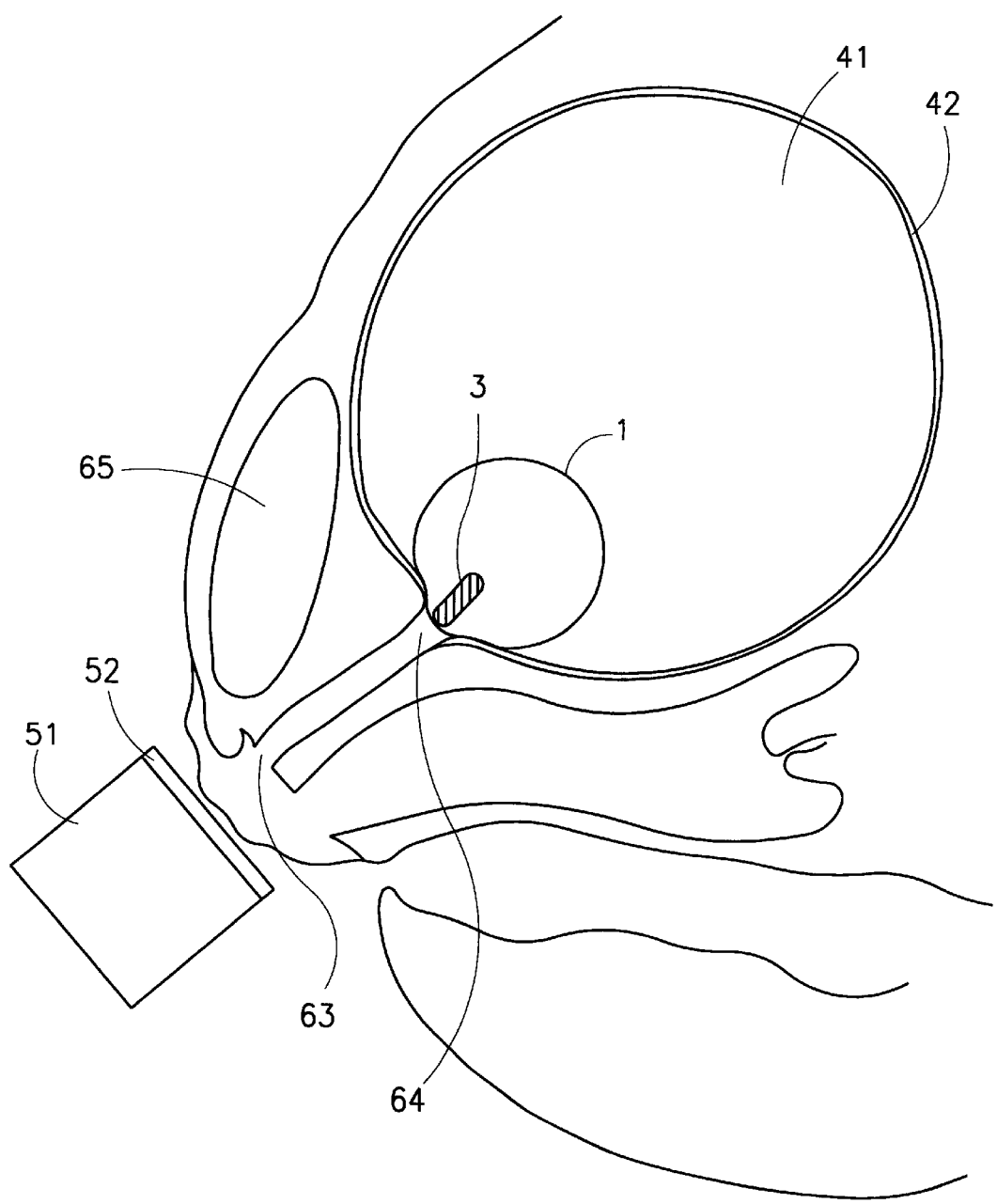
FIG. 12 shows use of a displacing member to displace a balloon into a sealing position within the urinary bladder.
Figure 13:
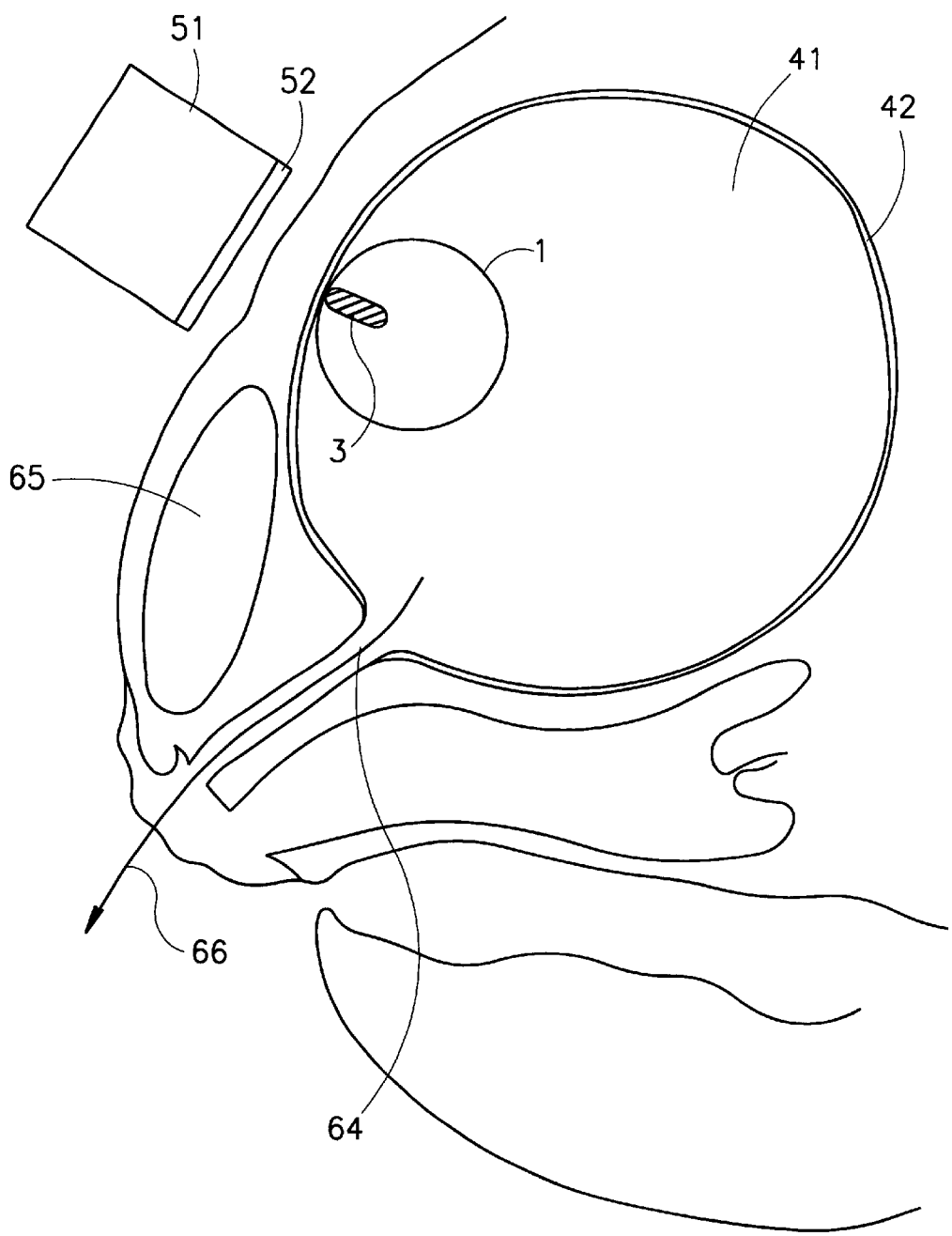
FIG. 13 shows use of a displacing member to displace a balloon from a sealing position in the urinary bladder.

FIGS. 12 and 13 show use of a displacing member 51 to position the balloon 1 at a desired location within the lumen 41 of an individual's urinary bladder 42. The displacing member 51 is located outside the individual's body and comprises a magnetable portion 52. The displacing member 51 is placed at a location on the surface of the individual's body so as to draw the balloon 1 from its initial location to the desired location.

FIG. 12 shows use of the balloon 1 for sealing the urinary bladder outlet in a female subject. Displacing member 51 is placed over the urethral meatus 63 such that, due to the magnetable portion 52 associated with the displacing member 51 and the magnetable portion 3 associated with balloon 1, the balloon is drawn into the bladder outlet 64. The balloon thus becomes lodged in the outlet and seals it. As the amount of urine in the bladder increases, a hydrostatic pressure is exerted on the balloon further lodging it in the outlet and reinforcing the seal. The invention is used similarly for sealing the urinary bladder outlet in male subjects.

As seen in FIG. 13, in order to open the urinary bladder for voiding, the magnetic displacing member 51 is placed over the upper edge of the pubic bone 65. Due to the magnetable portion 3 of the balloon 1, the balloon 1 is raised and dislodged from the bladder outlet 64 so as to allow voiding of urine as indicted by arrow 66. After voiding the balloon is redrawn into the bladder outlet 64 by the displacing member 51 so as to seal the outlet again as shown if FIG. 12.

Figure 14:
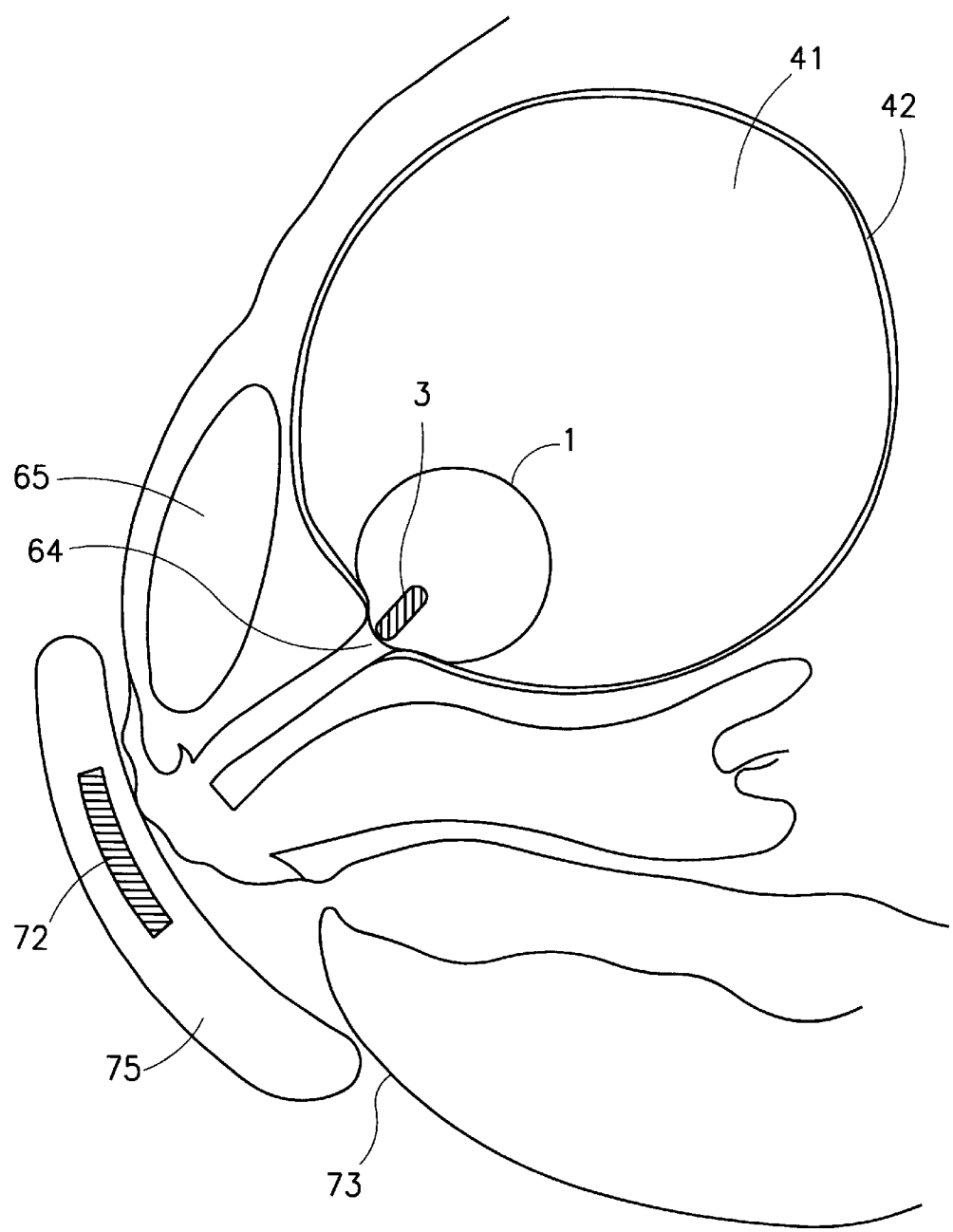
FIG. 14 shows use of an immobilizing member.

FIG. 14 shows use of an immobilizing member 71 comprising a magnetable portion 72 affixed to the surface 73 of the individual's body so as to maintain the balloon 1 at the desired location in the lumen 41 of the urinary bladder 42. The magnetable portion 72 of immobilizing member 71 may be enclosed in a coating 75 so as to form, for example, a hygienic pad. The immobilizing member 71 may be affixed to the surface 73 by means of tape, or by pressure applied to it by the individual's underwear.

The invention has been described with a certain degree of particularly only for the sake of clarity. However, several variations and modifications in the invention are possible without exceeding the scope and spirit of the invention as defined in the following set of claims.

What is claimed is:

1. A method for treating urinary incontinence in an individual comprising the steps of:
   a) inserting an expandable balloon into the individual's urinary bladder, the balloon having a wall, a lumen and a magnetizable portion wherein the balloon upon expansion has a specific gravity less than or equal to that of urine;
   b) expanding the balloon in the urinary bladder, and
   c) displacing the balloon into a sealing position with an external magnetizable displacing member for sealing the urinary bladder.

2. The method of claim 1, further comprising a step of displacing the balloon within the urinary bladder into an unsealing position for voiding the urinary bladder.

3. The method according to claim 2, wherein at least one of the one or more substances is a drug or antibiotic.

4. The method according to claim 1, wherein the magnetizable portion comprises one or more magnetizable particles in the lumen of the balloon.

5. The method according to claim 1, wherein the magnetizable portion of the balloon comprises one or more magnetizable particles attached to the wall of the balloon.

6. The method according to claim 1, wherein the magnetizable portion of the balloon comprises one or more magnetizable particles embedded in the wall of the balloon.

7. The method according to claim 1, wherein the balloon further comprises a self-sealing valve.

8. The method according to claim 1, wherein the balloon comprises means for storing one or more substances and releasing them into the urinary bladder.

9. The method according to claim 8, wherein the one or more substances are stored in the lumen of the balloon.

10. The method according to claim 8, wherein the one or more substances are stored in the wall of the balloon.

11. The method according to claim 8, wherein at least one of the one or more substances is a radioactive substance.

12. The method according to claim 1, wherein the balloon further comprises imaging means for imaging the urinary bladder.

13. The method according to claim 12, wherein the balloon comprises a transmitter for transmitting signals from the imaging means to a receiver.

14. The method according to claim 12, wherein the imaging means comprises a microvideo camera.

15. The method according to claim 12, wherein the imaging means is affixed to an outer surface of the balloon, embedded within a wall of the balloon, or affixed to an inner surface of the balloon.

16. The method according to claim 1, wherein the balloon further comprises at least one monitoring means for monitoring urinary bladder parameters and contents of the bladder.

17. The method according to claim 16, wherein the at least one monitoring means monitors a parameter of the urinary bladder selected from the group comprising:
   a) bladder pressure;
   b) urine temperature;
   c) urine density; and
   d) urine composition.

18. The method according to claim 16, wherein the balloon further comprises a transmitter for transmitting signals from the monitoring means to a receiver.

19. The method according to claim 16, wherein the monitoring means is affixed to an outer surface of the balloon, embedded within a wall of the balloon, or affixed to an inner surface of the balloon.

20. The method according to claim 1, wherein the balloon is inserted into the urinary bladder using an applicator fitted at an end thereof with a gripping device for releasably gripping the balloon.

21. The method of claim 20, wherein the gripping device comprises a plurality of flanges.

22. The method of claim 20, wherein the balloon comprises a magnetizable portion and the gripping device comprises a magnetizable portion.

23. The method according to claim 1, further comprising immobilizing the balloon with an immobilizing member, the immobilizing member comprising a magnetizable portion and being securable onto the individual'a body for immobilizing the balloon at a desired location in the individual's urinary bladder.

24. The method according to claim 23, wherein the immobilizing member is in the form of a hygienic pad positionable in the individual's underwear.

25. The method according to claim 1, wherein the balloon is expanded using an expanding device.

26. The method according to claim 25, wherein the expanding device comprises a syringe for injecting fluid into the balloon to expand the balloon.

27. The method according to claim 1, wherein the balloon comprises means for storing one or more substances and releasing them into the urinary bladder; and the method further comprises a step of loading one or more substances into the balloon.

28. The method according to claim 27, wherein at least one of the one or more substances is selected from the group consisting of:

a) a drug;

b) an antibiotic; and c) a radioactive substance.

29. The method according to claim 1, wherein the balloon comprises:

a) at least one monitoring means for monitoring urinary bladder parameters and contents of the bladder; and b) a transmitter for transmitting signals from the monitoring means to a receiver and the method further comprises transmitting signals from the monitoring means to the receiver.

30. The method of claim 29, further comprising at least one step selected from the group consisting of:

a) storing the signals in a computer memory;

b) displaying the signals on a display;

c) processing the signals in a computer processing unit;

d) storing results of the processing in a computer memory; and e) displaying results of the processing on a display.

31. The method according to claim 1, wherein the balloon further comprises:

a) imaging means for imaging the urinary bladder; and b) a transmitter for transmitting signals from the imaging means to the receiver; and the method further comprises transmitting signals from the imaging device to the receiver.

32. The method of claim 31, further comprising at least one step selected from the group consisting of:

a) storing the signals in a computer memory;

b) displaying the signals on a display;

c) processing the signals in a computer processing unit;

d) storing results of the processing in a computer memory; and e) displaying results of the processing on a display.

33. The method according to claim 1, wherein the balloon is filled with a compressible fluid and compressed before insertion into the bladder.

* * * * *